United States Patent [19]
Clark

[11] Patent Number: 5,991,017
[45] Date of Patent: Nov. 23, 1999

[54] INSPECTING THE SURFACE OF AN OBJECT

[75] Inventor: Mark Q. Clark, Salwick, United Kingdom

[73] Assignee: British Nuclear Fuels PLC, Cheshire, United Kingdom

[21] Appl. No.: 08/973,988

[22] PCT Filed: Jun. 15, 1995

[86] PCT No.: PCT/GB95/01394

§ 371 Date: Jan. 30, 1998

§ 102(e) Date: Jan. 30, 1998

[87] PCT Pub. No.: WO97/00438

PCT Pub. Date: Jan. 3, 1997

[51] Int. Cl.[6] .................................................. G01N 21/00
[52] U.S. Cl. .......................... 356/237; 356/445; 356/222; 356/229
[58] Field of Search .................... 356/237, 445, 356/222, 229

[56] References Cited

U.S. PATENT DOCUMENTS

| | | | |
|---|---|---|---|
| 4,806,776 | 2/1989 | Kley | 356/369 |
| 4,872,758 | 10/1989 | Miyazaki et al. | 356/369 |

FOREIGN PATENT DOCUMENTS

| | | |
|---|---|---|
| 0 048 072 | 3/1982 | European Pat. Off. . |
| 0 090 304 | 10/1983 | European Pat. Off. . |
| 0 284 630 | 10/1988 | European Pat. Off. . |
| 0 387 930 | 9/1990 | European Pat. Off. . |
| 0 413 817 | 2/1991 | European Pat. Off. . |
| 0 583 092 | 2/1994 | European Pat. Off. . |
| 2 666 884 | 3/1992 | France . |
| 2 057 675 | 4/1981 | United Kingdom . |
| 2 155 630 | 9/1985 | United Kingdom . |
| WO 88/04422 | 6/1988 | WIPO . |

*Primary Examiner*—Robert H. Kim
*Assistant Examiner*—Reginald A. Ratliff
*Attorney, Agent, or Firm*—Nixon & Vanderhye P.C.

[57] ABSTRACT

An arrangement for inspecting the surface of a rotating object (1) which includes object retaining means for retaining whilst rotating the object, means (3) for irradiating the surface of an object when retained and rotated by the object retaining means with a first beam of optical radiation, means (5) for irradiating the surface of an object when retained and rotated by the object retaining means with a second beam of optical radiation detectable as distinct from the first beam, detector means (7) for detecting radiation reflected by the surface of the object from the first beam and for detecting radiation reflected by the surface of the object from the second beam and a signal processor (15) for receiving signals produced by the detector means and for analysing such signals wherein the first beam and the second beam are of different wavelengths or in different wavelength bands and the detector means is capable of simultaneously receiving and detecting radiation received from the same irradiated area of the surface of the object from both the first beam and the second beam and producing a first output signal comprising components representing variations in reflection of the first beam from units of area within the said irradiated area of the object and a second output signal comprising components representing variations in reflection of the second beam from units of area within the said irradiated area of the object and wherein the signal processor is adapted to correlate components of the first output signal with the components of the second output signal whereby information about the reflectivity of units of area of the surface of the object is enhanced.

21 Claims, 2 Drawing Sheets

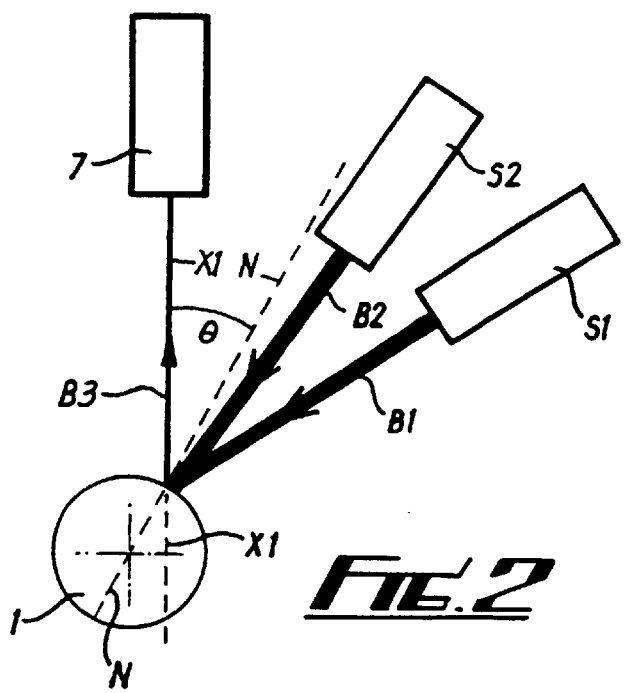
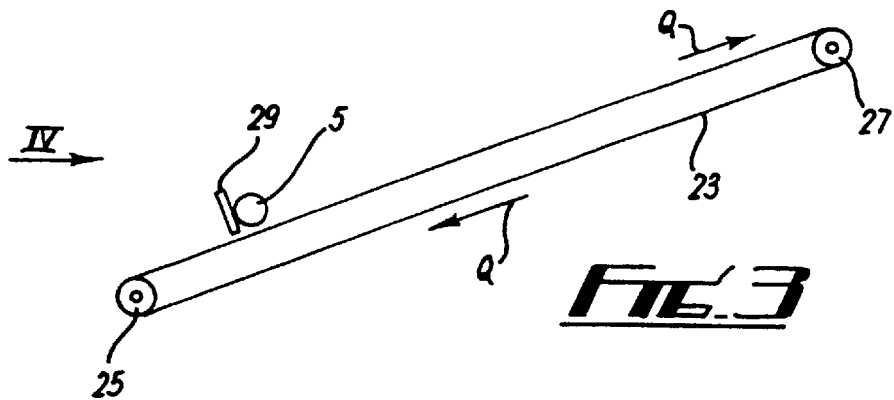
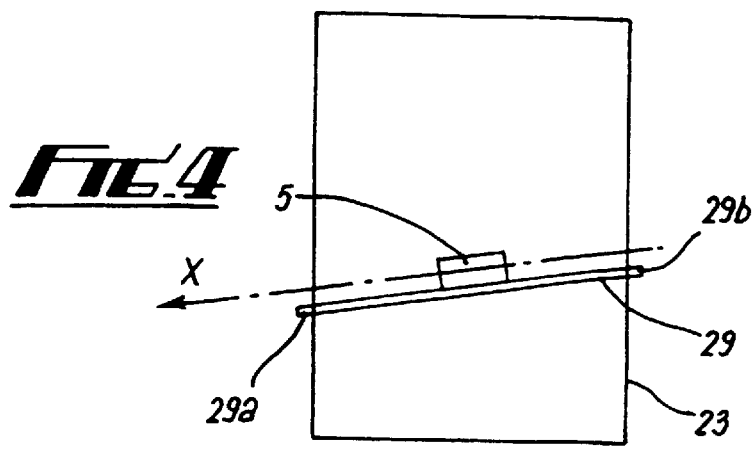

INSPECTING THE SURFACE OF AN OBJECT

BACKGROUND OF THE INVENTION

1. Field of the Invention

The present invention relates to apparatus and a method for inspecting the surface of an object.

2. Discussion of the Prior Art

Product surface inspection procedures are widely used in various industries. One such industry where careful surface inspection is essential is nuclear fuel production. Typically, nuclear fuel pellets are produced to high quality standards and after inspection following manufacture are loaded into tubes known as fuel rods or pins which are assembled together and in due course and loaded for use in a nuclear reactor. It is a customer requirement that inspection of all fuel pellets is carried out before loading into pins. This reduces the possibility of defective pellets causing pin damage when the pin is subject to high temperature and pressure in use.

At present, it is conventional for trained inspectors to perform nuclear fuel pellet inspections with the pellets held on trays. This manual inspection procedure has a number of disadvantages, viz:

(a) the standard of inspection is variable dependent upon the subjective judgement of the individual inspector, and is open to operator error;

(b) the inspector has to be close to the pellets; where the fuel pellets comprise MOX (mixed oxide) fuel pellets, eg comprising mixtures of uranium and plutonium oxides, this may be unacceptable from a safety point of view;

(c) the time and cost of the human work required to carry out the inspections is substantial.

Optical techniques for automatically inspecting objects such as nuclear fuel pellets are known in the prior art. For example, Applicants' prior EP 0 583 092 A1 describes such a technique using reflection of a laser beam spot by the inspected object.

One major problem which the known techniques using reflection of light are not capable of solving is that different surface flaw and defect types can reflect light in similar ways and this means that information about the defect or flaw provided by the reflected light may be limited. In some cases it may be difficult for the detection system to differentiate between different defect and flaw types or normal variation in surface appearance and flaws.

SUMMARY OF THE INVENTION

According to the present invention there is provided an arrangement for inspecting the surface of a rotating object which includes object retaining means for retaining whilst rotating the object, means for irradiating the surface of an object when retained and rotated by the object retaining means with a first beam of optical radiation, means for irradiating the surface of an object when retained and rotated by the object retaining means with a second beam of optical radiation detectable as distinct from the first beam, detector means for detecting radiation reflected by the surface of the object from the first beam and for detecting radiation reflected by the surface of the object from the second beam and a signal processor for receiving signals produced by the detector means and for analysing such signals wherein the first beam and the second beam are of different wavelengths or in different wavelength bands and the detector means is capable of simultaneously receiving and detecting radiation received from the same irradiated area of the surface of the object from both the first beam and the second beam and producing a first output signal comprising components representing variations in reflection of the first beam from units of area within the said irradiated area of the object and a second output signal comprising components representing variations in reflection of the second beam from units of area within the said irradiated area of the object and wherein the signal processor is adapted to correlate components of the first output signal with the components of the second output signal whereby information about the reflectivity of units of area of the surface of the object is enhanced.

The arrangement according to the present invention may optionally include one or more further means for irradiating the said surface each with a beam of optical radiation of a different wavelength or in a different wavelength band detectable as distinct from the other beams, the detector means being capable of simultaneously detecting radiation reflected by the surface from the respective beams and producing for each further beam an output signal comprising components representing variations in reflection of the further beam from units of area within the said irradiated area of the object.

The said arrangement may be provided to inspect the surface of the object to detect surface flaws such as cracks, chips, pits, inclusions and uncleaned surface areas.

The said first beam may comprise light of a first colour, eg red, and the second beam may comprise light of a second colour, eg green. Other beams may comprise light of other colours.

In addition, the first and second beams may be further differentiated by their different optical polarisations, or where delivered in pulsed beams, by their optical pulse lengths or pulse codes (the detection system as described below being arranged to receive synchronised signals to recognise the different pulses).

Desirably, at least one of the said beams has an angular beam divergence of 20 degrees or less. In one embodiment of the present invention another of the said beams has an angular beam divergence of more than 20 degrees, eg more than 45 degrees. In that embodiment, the said beam of greater divergence provides diffuse illumination of the object surface over an angle subtended at the source of greater than 90 degrees. The said beam of lower divergence may be applied to the surface of the object at an angle of incidence of less than 30 degrees to the tangent to the surface. In that embodiment radiation reflected along a direction substantially parallel to the normal to the surface at the point of incidence is that which is detected in the manner described hereinafter.

In another embodiment of the present invention a second radiation beam has, in addition to the first mentioned beam, an angular beam divergence of 20 degrees or less. In that embodiment, both of the said beams of low divergence angle are desirably applied at an angle of less than 45 degrees to the normal to the surface of the object at which they are incident. In that embodiment, radiation reflected along a direction at an angle, eg greater than 0 degrees and up to 60 degrees, eg 20 to 60 degrees, to the normal to the surface at the point of incidence is that which is detected in the manner described hereinafter.

The first means for irradiating may comprise a light source providing a beam of elongate shape, eg rectangular or oval, eg pencil shaped, cross-section, optionally together with means for focusing the beam onto the object whereby an illuminated line is formed on the surface of the object. In the said further embodiment described above another of the said means for irradiating may also form such an illuminated line on the surface or the object in a similar manner.

The first and second means, and any further means, for irradiating may each independently comprise a known coloured light source, eg a white light source together with a colour filter or a coloured light source, eg a gas discharge lamp such as a mercury lamp, or one or more semiconductor light emitting diodes (led), or luminescent, electroluminescent, eg dc electroluminescent, or one or more plasma panel cell emitters. Where one of the means for irradiating comprises a white light source together with a colour filter the light provided thereby may be arranged to illuminate the surface of the object diffusely. A fibre optic guide may be employed to conduct light from the source to the region where it is required to illuminate the surface of the object.

Desirably, the intensity of radiation provided by the different sources is adjustable so that different output intensities can be provided as selected by the user according to the appropriate system for the application. The wavelength bands of the output radiation of the different sources is also desirably interchangeable to provide a selection of an appropriate irradiation arrangement.

By providing two or more different arrangements for irradiating the same surface of the object under inspection at the same time two or more channels of information about the surface can be obtained simultaneously and these can be correlated in the ways described below to provide overall a greater output of information than any one of the channels individually. This enables surface detect and flaw types to be more easily recognised by known signal recognition techniques and for information about a given defect to be maximised by selection of the channel of information containing the greater amount of information about the particular defect, or by comparing and contrasting the signals detected in the different channels. These operations can be carried out by known signal processing techniques in the manner described below.

Although two-colour inspection systems are known in the prior art these have been used for other purposes and do not therefore detect, process and correlate the information reflected from the surface of the object by the multiple colour beams in the manner described herein.

The present invention is particularly applicable to the automatic inspection of nuclear fuel pellets. The pellets may comprise well known shapes, eg they may be hollow or solid right circular substantially cylindrical bodies. The ends may be flat surfaces or may be convex curves rather than flat surfaces. The pellets may for example be for use in either so called AGR or LWR types of nuclear reactor. The pellets may comprise uranium oxide optionally doped with one or more known additives, eg niobia or gadolinia. Alternatively, the pellets may comprise MOX pellets as referred to hereinbefore. In that case, the pellets will normally be within a containment such as a glovebox which confines the plutonium oxide thereby preventing outside contamination. The components of the apparatus according to the invention may be located outside such containment. The containment may include a window, eg made of a high quality glass, which allows the optical radiation to pass in and out of the containment to inspect the pellets therein. As only a small number of pellets need to be in the containment for inspection at any one time the window is not required to act as a radiation shield. Conventional neutron and gamma radiation shielding material can be provided around the components of the apparatus located outside the containment containing the pellets being inspected.

In the apparatus according to the present invention, the detector means may comprise a photodetector having a first set of photodetector cells adapted to detect only radiation reflected from the first beam (not from the second beam) and a second set of photodetector cells adapted to detect only light in a different given wavelength band reflected from the second beam. Optionally, a third set of photodetector cells may be provided to detect only light reflected in a further different wavelength band from a third beam. In practice, as will be apparent to those familiar with photodetector devices, the photodetector cells may be discrete cells or alternatively regions of a single integral detector.

The detector means may include a linescan photodetector which has a single, double or triple row of photosensitive cells. The detector means may also include a lens or arrangement of lenses which focuses reflected radiation from a line on the inspected object onto the linescan photodetector whereby each cell in the row or both or each of the rows of the photodetector corresponds to a point on the line of the inspected object.

Where the linescan photodetector comprises a double row of photodetector cells one of the rows may have cells adapted to detect only radiation reflected from the first beam and the other may have cells adapted to detect only radiation reflected from the second beam. Where the linescan photodetector comprises a single row of cells alternate cells in the row may be adapted to detect radiation reflected only from the first beam and only from the second beam respectively. For example, alternate cells may be red and green light detectors. Further cells sensitive to another colour may be included between each pair of red and green light detectors.

If the inspected object comprises a right circular substantial cylinder it may be rotated on its axis at a surface rotational speed of greater than 10 mm per sec, eg greater than 50 mm per sec, eg about 75 mm per sec. The surface lines inspected in the manner described using a linescan photodetector will be different adjacent lines, taken in sequence, making up the complete revolving surface. The complete image of the revolving surface therefore consists of a multiplicity, eg several hundred, image lines captured sequentially, each line representing information concerning a row of points on the line. Thus, the complete image comprises a set o signals representing individual pixels which are the individual points on the lines formed on the surface.

In the apparatus according to the present invention simultaneous rotation and translation of the objects to be inspected may be carried out in a known way by using apparatus comprising a continuous belt which may be moved along a track which is inclined relative to the horizontal plane, and a plate extending across the surface of the belt. Desirably, the angle of the plate relative to the side edges of the belt is adjustable. Objects, eg cylindrical nuclear fuel pellets, are fed onto the belt above the plate and become supported on the belt by the plate. Movement of the belt provides rotation of the object about its axis and deviation from the horizontal plane of the line representing the projection of the edge of the plate across the belt allows lateral translational movement of the objects by sideways slippage. The direction of the translation may be in a positive or negative sense depending on whether the plate is tilted downward to the left or to the right. The speed of rotation of the objects may be adjusted by adjusting the speed of the belt and the translational movement may be adjusted by adjusting the angle of the plate relative to the edges of the belt.

Alternatively, the translational movement may be produced by varying the angle of the line of belt movement, relative to a fixed position of the plate. In both alternatives it is the angle between the belt and the plate which provides the degree of translation. The means for rotating the objects may in another form of the present invention comprise as described in Applicants' EP 0583092A adjacent rollers and means for rotating the rollers in the same sense whereby objects placed on the rollers rotate on their axes with the rollers. The rollers may be mounted on a base which may be moved at constant speed by a suitable linear actuator in a known way along an axis, eg by a leadscrew providing movement along an axis parallel to the axes of the rollers and the object thereon. At the end of traverse provided by the actuator the linear movement may be reversed whereby the base is returned to a re-start position.

A plurality of objects, eg two to five objects, may be placed on the same rollers for inspection by the apparatus according to the present invention in the form including rollers. Such objects may each have its own dedicated inspection station and inspection arrangement comprising projection means and detection means. The objects may be placed together on the rollers. Alternatively, one inspection arrangement may be shared between two or more objects. For example, each object in the plurality may be inspected in turn on the rollers whilst another is being removed and replaced and so on.

In the form of the invention including rollers the objects may be placed on and removed from the rollers by a pick and place machine. The objects may be obtained from a pick up position and moved in a lateral direction substantially perpendicular to the axes of the rollers when they are placed on and subsequently removed from the rollers. The objects may be inspected and the results of the inspection may be obtained prior to removal from the rollers. If the result of the inspection is that the object is acceptable it may be removed by the pick and place machine to an acceptance location. If the result is that the object is unacceptable it may be removed by the pick and place machine to a reject location. Suitable signals from the inspection apparatus may be applied to operate the pick and place machine through a suitable known controller, eg a programmable logic controller (plc), to control where the objects are deposited. A plurality of objects may be deposited together at the acceptance location and/or at the reject location as appropriate.

In the automatic handling of nuclear fuel pellets, the pellets may be conveyed to a pellet inspection apparatus for inspection in accordance with the present invention any the Applicants' so-called "Cushion Transfer" (™) technique which is described in UK Patent Specification No. GB 2223998A.

In the form of the invention comprising rollers the nuclear fuel pellets may be conveyed to a pick up location and may be transported away from an acceptance location by Cushion Transfer conveyers.

In the form of the invention wherein pellets are rotated and translated by a belt and plate, a single Cushion Transfer conveying track may be divided into a plurality of tracks, eg five tracks, each track feeding pellets to its own inspection station. Each station may include its own means for rotating and translating the pellets and its own projection and detection means. The pellets moving along the different tracks may be recombined onto one track after inspection, although pellets bearing a detected defect may be automatically removed from their track, eg by operating a chute, after passing through the inspection apparatus. This operation may be carried out by counting the number of pellets introduced into the inspection apparatus, recording the count number of defective pellets and counting the number of pellets leaving the apparatus until the defective pellet is reached. These operations may be carried out automatically by use of counters and a count recorder. Such a system is known as "first in first out" ("fifo").

Desirably, each inspection apparatus is calibrated in use from time-to-time using calibration pellets of known dimensions having a defect-free surface and also defects of known dimensions.

BRIEF DESCRIPTION OF THE DRAWINGS

Embodiments of the present invention will now be described by way of example with reference to the accompanying drawings, in which:

FIG. 2 is a schematic end view of an alternative lighting arrangement for use in the apparatus shown in FIG. 1;

FIG. 3 is a side view of an arrangement for providing rotation and translation of an object using the apparatus shown in FIG. 1 or FIG. 2.

FIG. 4 is a front view (in the direction IV—IV shown in FIG. 3) of the arrangement shown in FIG. 3.

DETAILED DISCUSSION OF PREFERRED EMBODIMENTS

Figure 1:
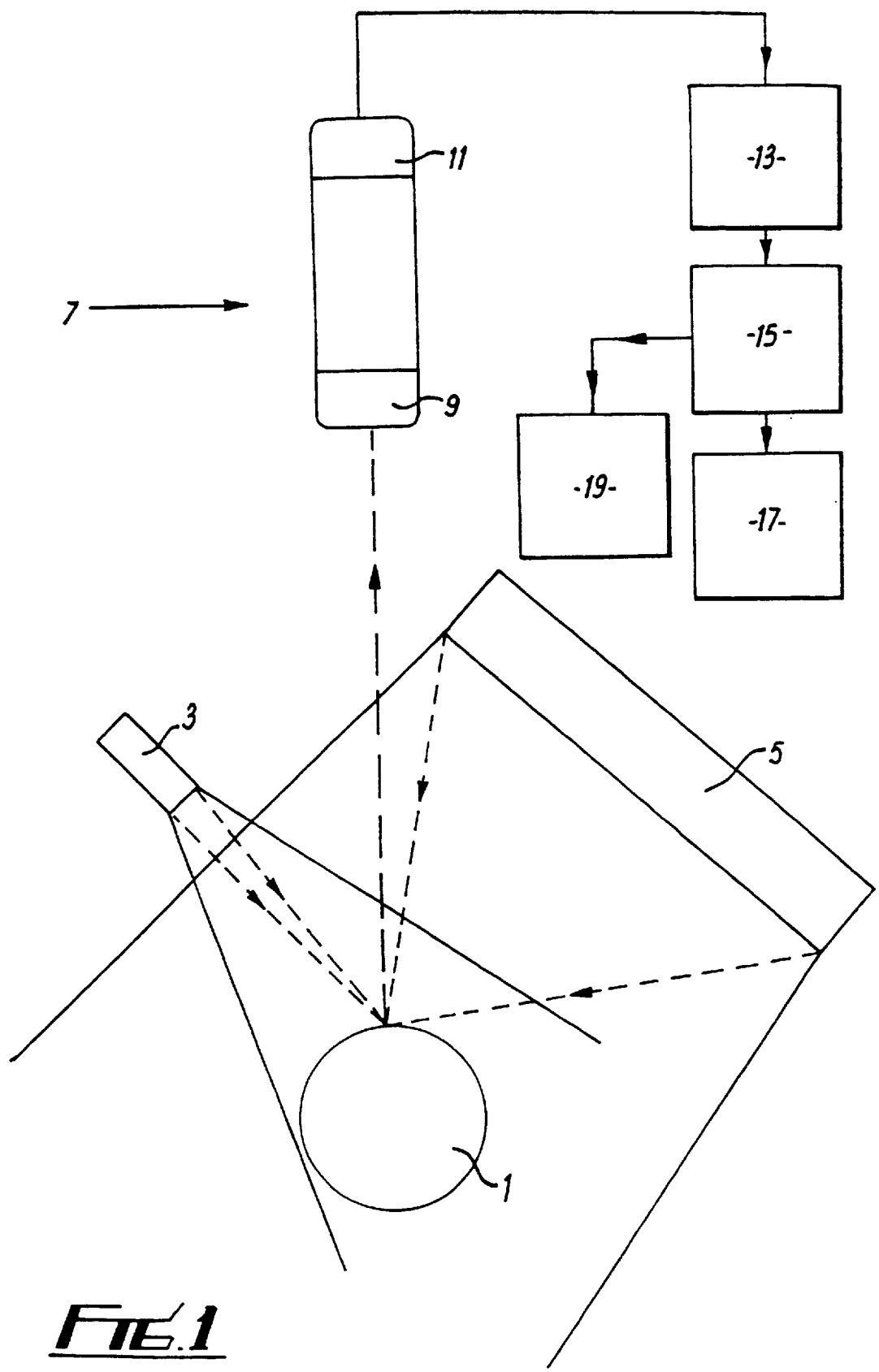
FIG. 1 is a schematic diagram, partly in block circuit diagram form, of an inspection apparatus embodying the present invention.

FIG. 1 shows a layout of an arrangement comprising an inspection apparatus embodying the present invention. A right circular substantially cylindrical object 1, eg a nuclear fuel pellet, is rotating about its own axis and is slowly moving in a direction X along that axis by an arrangement described below with reference to FIGS. 3 and 4. The object 1 is illuminated by light from a first light source 3 and also by light from a second light source 5. The first source 3 provides light of a first colour, eg red, in a relatively narrow beam, eg subtending an angle of less than 5 degrees at the source 3. The light from the source 3 strikes the object at a narrow angle, eg less than 30 degrees, to the axis thereof. The second source 5 provides light of a second colour, eg green, in a wide angle beam, eg subtending an angle of more than 90 degrees at the source 5, so that much of the light is incident on the object 1 at angles greater than 30 degrees to the axis. The source 3 therefore provides high contrast lighting and the source 5 provides diffuse, low contrast lighting. The sources 3, 5 may each include a filter (not shown) to ensure that the light produced is in a suitably narrow wavelength band. An image of the illuminated object 1 is captured by a camera 7. In the camera 7, a lens 9 focuses light reflected from the object 1 onto a linescan photodetector 11. The field of view of the camera 7 is deliberately restricted such that only a light from a given line on the illuminated object 1 is received so that an image of that line is formed on the photodetector 11.

The photodetector 11 comprises arrow of photocells. Individual photocells in the row are alternately sensitive to red and green light. Thus, some photocells in the row will detect a red image of the selected line on the object 1 and alternate photocells in the row will detect a green image of the same selected line on the object 1.

The photodetector 11 is controlled by a controller 13 which also receives and digitises the outputs from the photodetector 11. The outputs provided from the controller 13 are processed by a signal processor 15 and the results are displayed on a display 17. In practice, the signal processor 15 may comprise a digital personal computer and the controller 13 may comprise a printed circuit board for connection to the computer. One or more additional circuit boards, eg an accelerator board to give enhanced computer signal processing speed, may also be added. For example, the photodetector 11 may comprise an E&G Reticon LC1922 Linescan Camera employed together with a Data Translation DT 2856 Linescan Controller Board. The DT 2856 supports DT-Connect which is a bus providing high speed transfer of data from the DT 2856 Board to other boards connected to the computer. An Alacron FT 200 may be used as an accelerator board. The personal computer may comprise for example an 80386 or 486 based IBM PC.

In order to form images of the entire curved surface of the object 1 a sequence of line images is formed on the photodetector 11 in the manner described above. As the object 1 rotates, the line images formed will correspond to successive lines across the object 1 parallel to the axis of the object 1. Eventually, these lines will cover an area scan comprising one revolution of the curved surface.

The smallest unit of area in each captured line image is a pixel and corresponds to a unit of area along the line on the object 1 detected by the camera 7. The width of the pixel is determined by the width of the photocells in the photodetector and the magnification of the camera 7. The height of each pixel in the line image is dependent on the rotational speed of the object 1 and the scanning rate of the photodetector 11 by the controller 13.

Where an apparatus as shown in FIG. 1 is employed to detect defects on or adjacent to the surface of a nuclear fuel pellet, ie the pellet is an object 1 as in FIG. 1, the detection of surface cracks is especially important. Cracks are produced by the internal stresses that occur during sintering to produce the pellet. Cracks can weaken pellets to the extent where they may break into several parts with a possibly detrimental effect on in-reactor performance. All pellets must therefore be inspected for cracking and cracked pellets that exceed safe limits must be rejected.

So-called "end capping" is a particular type of cracking that occurs near the pellet ends in nuclear fuel pellets and characteristically comprises several circumferential cracks that extend around the circumference of the pellet. This severely weakens the attachment of the pellet end to the rest of the pellet.

The most distinctive feature of surface cracks under inspection by a beam of light is that they appear dark owing to the crack being much deeper than its width. Light falling on the crack undergoes several reflections before emerging. Each reflection greatly reduces the light intensity. For the most reliable crack detection, the crack should appear as dark as possible in the captured image. Reducing the pixel size makes narrower racks detectable at the expense of processing more data and longer capture times. A crack of sub-pixel width crossing a pixel lowers the average intensity seen for that pixel. If this value is then below the crack detection threshold that pixel is seen as a crack pixel. Setting the threshold closer to the signal level from a normal pellet makes narrower cracks detectable. The threshold setting is a compromise between extracting as much information as possible from the image and not mistaking noise for cracks. If the noise level is low more information can be safely extracted from the image.

The noise in the thresholded image is dependent on the lighting arrangement. High contrast lighting from the source 3 is used to give information on the orientation of the surface being illuminated/inspected. This allows the edges of chips to be detected due to the change in surface orientation. A high contrast lit image also contains information about the orientation of individual grain facets. This makes the image appear grainy or noisy when viewed as a picture on the display 17.

Low contrast lighting from the source 5 makes the normal pellet surface appear smooth with little noise in the captured image. As described above, the reduced noise allows the setting of the defect threshold much closer to the average level of the pellet surface allowing detection of smaller cracks. With dry ground pellets the low contrast lighting hides cracks and the alternative embodiment described below with reference to FIG. 2 may be employed instead.

The apparatus shown in FIG. 1 can be employed to measure the axial and circumferential length components of cracks and to combine them to determine the extent of cracking. Other pellet surface defects as follows may be recognised and measured by the apparatus:

Chips These are typically shallow regions of missing material in the surface of the pellet. Different parts of the chip will reflect in different ways depending on the position of the light source.

NCUs Areas on the surface of the pellet which are smooth because they have not been surface treated are known as NCUs. They may appear lighter or darker than normal surface areas depending on the lighting system.

Pits and Pores Pits are circular or near circular cavities in the surface of the pellet. They are distinguished from pores by the bottom of the cavity being visible. The apparatus may inspect both pits and pores. Pits and pores can be distinguished from cracks by their height/width aspect ratio which is near to unity. The aspect ratios of cracks are larger.

Inclusions Inclusions are regions of material different from the base pellet material. This material is typically either $U_3O_8$ or metallic uranium formed during processing. These materials can appear darker or lighter than the base material and are visible in the image. Thus, the processor 15 is employed to recognise regions of darker or lighter reflectance in the image.

The following inspection and defect recognition and control procedure may be carried out using the apparatus shown in FIG. 1. Firstly, an image is captured by the photodetector 11 and controller 13. Next, the pixel components of the image are compared with a pre-set threshold in the signal processor 15. Next, a known 3 by 3 local operator function is applied to the image signal produced in the processor 15. This has the effect of removing individual noise pixels whilst slightly dilating (enlarging) any crack-like features. The local operator function assigns a new bright or dark value to each pixel based on the pixel's previous value and the previous values of the eight pixels surrounding it. Next, the image signal is analysed in the processor 15 for the axial and circumferential components of cracks, and also chips, pits, pores, NCUs and inclusions. These various defects are recognised and measured by the signal processor 15 in the following ways.

Firstly, different types of defects may be distinguished by comparing in the signal processor 15 the results from the two different lighting and imaging systems employed together, ie from the image formed in the photodetector 11 by illumination of the object 1 by the red light source 3 and from the image formed in the photodetector 11 by illumination of the object 1 by the green light source 5. For example, (a) cracks and pits can appear dark under both lighting systems;

(b) inclusions can appear light under both lighting systems;

(c) NCUs can appear dark under one (red) lighting system and light under the other (green);

(d) the leading edge of a chip can appear light under one lighting system (red) and grey (ie intermediate between light and dark) under the other lighting system (green);

(e) the trailing edge of a chip can appear dark under one lighting system (red) and grey under the other system (green);

(f) the normal pellet surface (ie containing no defects) can appear grey under both lighting systems.

Thus, the first lighting system (red) which provides near tangential lighting of the surface of the object 1, is convenient for chip detection. The second lighting system (green), produces a soft low contrast illumination that reduces the effects of surface finish and damage. This provides different information that can be contrasted with information from the first system to allow the different types of defect feature to be readily distinguished by the processor 15.

Where any one of the sizes or dimensions of any of the detected defect types exceeds the pre-set threshold a reject signal is generated by the signal processor 15. The reject signal is fed to a known reject controller 19 which selectively removes the pellet inspected from the stream of pellets. Where no reject signal is generated the pellet is allowed to continue in the main stream of pellets for subsequent loading into a tube comprising a fuel pellet pin.

FIG. 2 shows an alternative lighting arrangement which may be used in conjunction with the detection arrangement shown in FIG. 1, ie camera 7, photodetector 11, controller 13 and signal processor 15. In FIG. 2 the camera 7 is located to view along an axis X1 a line on the surface of the object 1 produced by light from two different sources S1 and S2. The axis X1 is offset at an angle ζ relative to the normal N to surface at the line of illumination. Both light sources S1 and S2 provide high contrast lighting beams B1 and B2 respectively. One of the sources S1 is arranged such that the beam B1 is provided at an angle θ relative to the normal N and is specularly reflected as a beam B3 to the camera 7 by the surface of the object 1 to the camera 7. The other source S2 is arranged such that the beam B2 is provided at a small angle, eg less than 10 degrees, to the normal N such that light only reaches the camera 7 substantially from non-specular reflections from the beam B2.

Using the arrangement illustrated in FIG. 2 areas of missing material on the surface of the pellet 1, eg due to pits, chips, cracks and pores, are darkened in the image produced by light from source S1 and are easily thresholded. NCUs appear very bright. In the image produced by light from source S2 chips are partly visible and NCUs are of darker or average intensity. Bright inclusions are brighter in both images.

A third light source may optionally be employed in the lighting arrangements shown in FIGS. 1 and 2 to provide light of a third colour. The light from the third source forms a line image on the surface of the object 1 co-incident with those from the other two sources in each arrangement. With the third light source employed the photodetector is sensitive, in one of the ways described above to the light from the third source.

FIGS. 3 and 4 show one form of device for rotating and translating the objects 1 for use with the apparatus shown in FIG. 1 or FIG. 2.

A continuous rubber belt 23, driven at a constant velocity by a servo motor (not shown) moves in the direction of the arrows Q around rollers 25, 27. The belt 23 is inclined by virtue of the roller 27 being at a height above the roller 25. An object 1 to be inspected is supported on the belt 23 by a plate 29. The angle of the plate 29 relative to the side edges of the belt 23 is adjustable but in FIG. 4 the angle is adjusted so that one end 29a is lower than the other end 29b. The object 1 is caused to rotate by the movement of the belt 23 and to be moved laterally or translated in a direction X parallel to its axis by lateral slippage down the plate 29. If the angle of the plate 29 is changed so that the end 29a is above the end 29b then the lateral movement of the object 1 is in the opposite direction.

I claim:

1. An arrangement for inspecting the surface of a rotating object, the arrangement comprising:
   a plate retaining the object during rotation,
   a first source irradiating the surface of the object with a first beam of optical radiation and a second source irradiating the surface of the object with a second beam of optical radiation, the first and second beams of optical radiation being detectably distinct, the first and second beams being of different wavelengths or different wavelength bands,
   at least one detector detecting radiation of the first beam reflected off the surface of the object and detecting radiation of the second beam reflected off the surface of the object from the same irradiated area, the at least one detector producing a first output signal comprising components representing variations in reflection of the first beam from units of area within said irradiated area and a second output signal comprising components representing variations in reflection of the second beam from units of area within the irradiated area, and
   a signal process, responsive to the first output signal and the second output signal, correlating the output signals to enhance information about the reflectivity of units of area of the object and providing a correlated output, the correlated output containing reflectivity information indicating whether a defect is present in the irradiated area.

2. An arrangement according to claim 1 in which a series of successive line images are formed on the at least one detector, the line images being formed of units of areas, pixels.

3. An arrangement according to claim 2 in which the light level of the pixel is determined and compared with a threshold, a pixel darker than the threshold being seen as a crack pixel.

4. An arrangement according to claim 1 in which the object is irradiated by a high contrast beam and a low contrast beam.

5. An arrangement according to claim 4 in which the high contrast beam is provided by a beam applied to the surface of the object at an angle of incidence of less than 30° to the tangent to the surface.

6. An arrangement according to claim 4 in which the low contrast beam is provided by a beam having an angular divergence of greater than 45°.

7. An arrangement according to claim 4 in which detected pixels are determined by the signal processor as dark, light or grey (intermediate) and a determination of defect type is made based on the pixel determination for the first and second output signals.

8. An arrangement according to claim 7 in which a dark pixel for both high contrast and low contrast beams is taken as indicative of a crack or pit.

9. An arrangement according to claim 7 in which a dark pixel from the high contrast beam and light pixel from the low contrast beam is taken as indicative of an NCU.

10. An arrangement according to claim 7 in which a light pixel for both high and low contrast beams is taken as indicative of an inclusion.

11. An arrangement according to claim 7 in which a light pixel from the high contrast beam and a grey pixel from the low contrast beam is taken as indicative of the leading edge of a chip.

12. An arrangement according to claim 7 in which a dark pixel from the high contrast beam and a grey pixel from the low contrast beam is taken as indicative of the trailing edge of a chip.

13. An arrangement according to claim 7 in which a grey pixel from both high and low contrast beams is taken as indicative of a normal surface.

14. An arrangement according to claim 4 in which pixels are compared with a pre-set threshold, a known 3 by 3 operator function is applied to remove individual noise pixels and enlarging crack features, the local operator assigning a new light or dark value to each pixel based on the previous value of that pixel and the previous values of the eight surrounding pixels, analysing the axial and circumferential components of cracks and determining defect type.

15. An arrangement according to claim 1 in which the object is irradiated by a first and second high contrast beam.

16. An arrangement according to claim 15 in which the at least one detector is located at an axis X1 at an angle A relative to the normal of the part of the surface being irradiated, the first light beam source being provided at an angle A to the normal on the opposing side to the at least one detector, the second light beam source being provided at an angle B to the normal on the opposing side to the at least one detector, angle B being less than 45° to the normal and less than angle A.

17. An arrangement according to claim 15 in which detected pixels are determined by the signal processor as dark, light or grey (intermediate) and a determination of defect type is made based on the pixel determination for the first and second output signals.

18. An arrangement according to claim 17 in which a dark pixel from the first light beam and a light pixel from the second light beam is taken as indicative of material missing from the surface, for instance a pit, chip, crack or pore.

19. An arrangement according to claim 17 in which a light pixel from the first light beam and a grey or dark pixel from the second light beam is taken as indicative of a NCU.

20. An arrangement according to claim 17 in which a light pixel from both firs and second light beams is taken as indicative of a bright inclusion.

21. An arrangement for inspecting the surface of a rotating object, the arrangement comprising:

a means for retaining the object during rotation, a means for irradiating the surface of the object with first and second beams of optical radiation, the first and second beams of optical radiation being detectably distinct, the first and second beams being of different wavelengths or different wavelength bands, detector means for detecting radiation of the first beam reflected off the surface of the object and for detecting radiation of the second beam reflected off the surface of the object from the same irradiated area, the detector means producing a first output signal comprising components representing variations in reflection of the first beam from units of area within said irradiated area and a second output signal comprising components representing variations in reflection of the second beam from units of area within the irradiated area, and a signal processor means, responsive to the first output signal and the second output signal, for correlating the output signals to enhance information about the reflectivity of units of area of the object and providing a correlated output, the correlated output containing reflectivity information indicating whether a defect is present in the irradiated area.

* * * * *